(12) United States Patent
Bacon

(10) Patent No.: US 9,365,342 B2
(45) Date of Patent: Jun. 14, 2016

(54) METERING DEVICE AND DISPENSING CONTAINER

(76) Inventor: Raymond John Bacon, Petersfield (GB)

(*) Notice: Subject to any disclaimer, the term of this patent is extended or adjusted under 35 U.S.C. 154(b) by 32 days.

(21) Appl. No.: 13/820,590

(22) PCT Filed: Sep. 5, 2011

(86) PCT No.: PCT/GB2011/051657
§ 371 (c)(1),
(2), (4) Date: Mar. 21, 2013

(87) PCT Pub. No.: WO2012/028889
PCT Pub. Date: Mar. 8, 2012

(65) Prior Publication Data
US 2013/0168415 A1  Jul. 4, 2013

(30) Foreign Application Priority Data
Sep. 3, 2010  (GB) .................................. 1014645.4

(51) Int. Cl.
| A61M 15/00 | (2006.01) |
| B65D 83/00 | (2006.01) |
| B65D 83/20 | (2006.01) |
| B65D 83/54 | (2006.01) |
| G01F 11/04 | (2006.01) |
| B65D 83/38 | (2006.01) |
| F16K 7/06 | (2006.01) |
| A61M 39/28 | (2006.01) |
| B65D 83/42 | (2006.01) |

(52) U.S. Cl.
CPC ......... *B65D 83/0055* (2013.01); *A61M 15/009* (2013.01); *A61M 15/0065* (2013.01); *A61M 15/0066* (2014.02); *B65D 83/206* (2013.01); *B65D 83/207* (2013.01); *B65D 83/38* (2013.01); *B65D 83/546* (2013.01); *G01F 11/04* (2013.01); *A61M 39/283* (2013.01); *B65D 83/42* (2013.01); *F16K 7/068* (2013.01)

(58) Field of Classification Search
CPC ............................. A61M 39/283; F16K 7/068
USPC ....................................... 222/207, 394; 251/4
See application file for complete search history.

(56) References Cited

U.S. PATENT DOCUMENTS

| 3,001,524 A | * | 9/1961 | Maison et al. ........... 128/200.23 |
| 3,187,748 A |  | 6/1965 | Mitchell et al. |
| 3,768,704 A | * | 10/1973 | Beguin ......................... 222/207 |
| 3,858,771 A | * | 1/1975 | Bret et al. .................... 222/402.2 |
| 4,771,918 A | * | 9/1988 | Haggart ......................... 222/95 |
| 4,892,232 A | * | 1/1990 | Martin ......................... 222/207 |
| 5,265,765 A | * | 11/1993 | Maier ................... B65D 83/62 222/105 |

(Continued)

FOREIGN PATENT DOCUMENTS

| EP | 20130 562 | 12/2009 |
| WO | WO 2008/023018 | 2/2008 |

OTHER PUBLICATIONS

International Search Report for PCT/GB2011/051657, mailed Nov. 18, 2011, Schork, Willi.

*Primary Examiner* — Daniel R Shearer
(74) *Attorney, Agent, or Firm* — Nixon & Vanderhye P.C.

(57) ABSTRACT

The invention relates a metering device for fluids from a containment volume. The metering device is a means to dispense metered volumes of fluids such as detergents, medicaments, lotions and the like. The invention further provides a container for fluid material to be dispensed in metered doses.

11 Claims, 6 Drawing Sheets

(56) References Cited

U.S. PATENT DOCUMENTS

| | | | |
|---|---|---|---|
| 5,707,038 A * | 1/1998 | Cocatre-Zilgien | 251/4 |
| 6,422,234 B1 * | 7/2002 | Bacon | A61M 15/0091 128/200.14 |
| 6,866,038 B2 * | 3/2005 | Bacon | F16K 7/068 128/200.14 |
| 7,225,805 B2 * | 6/2007 | Bacon | A61M 15/009 128/200.14 |
| 7,469,874 B2 * | 12/2008 | Akahori | 251/7 |
| 7,721,731 B2 * | 5/2010 | Bacon | A61M 15/0095 128/200.14 |
| 2004/0055596 A1 | 3/2004 | Bacon | |
| 2010/0224185 A1 | 9/2010 | Anderson et al. | |

\* cited by examiner

METERING DEVICE AND DISPENSING CONTAINER

This application is the U.S. national phase of International Application No. PCT/GB2011/051657, filed 5 Sep. 2011, which designated the U.S., and claims priority to GB Application No. 1014645.4, filed 3 Sep. 2010, the entire contents of each of which are hereby incorporated by reference.

This invention relates to a metering device and also a container for materials to be dispensed in metered doses.

It is known to use kink valves to release a dose of material metered in, for example, an aerosol valve, as in a metered dose inhalant dispenser. Such a valve is shown in EP 1 298 065 B1.

It is also known to meter a dose by means of a fixed volume of tube between two kink valves.

As used herein "kinking" in respect of a tube means bending the tube to such an extent that it collapses on itself, constricting its internal passage and thus a kink valve provides a valve function by means of closing off a tube through bending and opening through relatively straightening the tube.

Such use of kink valves has been in respect of medicament carried in an evaporative medium and under vapour pressure from the medium. It is desirable to dispense and meter fluids that are not directly propelled by a propellant.

One object of forms of the present invention is to provide a metering device or a container for materials to be dispensed in metered doses.

According a form of the present invention there is provided metering device for fluids from a containment volume the metering device comprising:
  an exit from the containment volume though which the fluid material is pressurised above ambient pressure,
  a metering chamber,
  a first valve for allowing a dose of the fluid material to flow from the exit into the metering chamber and fill the chamber to meter the dose,
  a dispensing outlet open to ambient pressure,
  a second valve allowing the dose of fluid material in the metering chamber to flow from metering chamber to the dispensing outlet and
  manually operable means for co-ordinating action of the valves whereby when the first is open for filling the metering chamber the second is closed and vice versa.

The metering device of this form of the invention may be fitted onto a container which contains fluid that is pressurised above ambient pressure. Actuating the metering device using the manually operable means will result in the metered volume to be dispensed. The metered volume is determined by the volume of the metering chamber between the two valves.

Alternatively described, the exit from the containment volume is the point at which the fluid material is pressurised above ambient pressure.

According to another aspect of the invention there is provided a container for fluid material to be dispensed in metered doses, the container comprising:
  a containment volume,
  an exit from the containment volume through which the fluid material is pressurised above ambient pressure,
  a metering chamber,
  a first valve for allowing a dose of the fluid material to flow from the exit into the metering chamber and fill the chamber to meter the dose,
  a dispensing outlet open to ambient pressure,
  a second valve allowing the dose of fluid material in the metering chamber to flow from metering chamber to the dispensing outlet and
  manually operable means for co-ordinating action of the valves whereby when the first is open for filling the metering chamber the second is closed and vice versa.

Whilst it is envisaged that in embodiments of the invention the containment volume could be arranged above the metering chamber in use, whereby the pressure above ambient is hydrostatic and the fluid flows from the containment volume to the metering chamber and from the metering chamber to the dispensing outlet by gravity; in various embodiments the fluid is pressurised by gas or mechanical pressure.

In certain embodiments, the containment volume will in effect be the entire volume of the container, such as where the fluid material is held in the container under pressure exerted by a gas also contained with the fluid. The gas may be in contact with the fluid or separated from it by a piston, diaphragm or the like. Alternatively, in other forms of the invention, the containment volume may be delimited within the container by a piston or diaphragm provided on its side opposite from the fluid with mechanical means acting on it to pressurise the fluid; in forms of the invention the mechanical means can be a spring, or other biasing means, which will occupy volume within the contents not available to be part of the containment volume. In another embodiment, a resilient diaphragm, elastic membrane, bellows or bellows bottle or the like may be employed to delimit the containment volume within the container. In an alternative, the containment volume may take the form of a flexible bag container with compression means such as pressurised gas or mechanical means.

When the containment volume is pressurised, it may be desirable to isolate the pressurised containment volume from the metering device during storage, for example by reducing the pressure, preferably by reducing the pressure to that of ambient pressure. This may be achieved by several means, including controlling the means for pressurising the containment volume, or in an alternative having a third valve in line with the pressurised containment volume, being placed between the containment volume and the metering device. This third valve may simply be an open/close valve. In this embodiment of the invention, operation of the means for isolating the pressure of the containment volume from the metering device may be achieved by any suitable means, for example, it may be linked to the closure means of the container. The closure means may be a cap, lid, screw-top, cover or any other suitable means. In this aspect, the opening of the closure means may cause the pressure of the containment volume to rise, or it may open the third valve, allowing the containment volume to access the metering device.

Whilst the metering chamber can be of fixed volume, particularly where it empties by gravity, it may also be expansible from an empty state to a maximum, metering volume. In the latter case, it will normally be a resilient or compliant chamber. A resilient or compliant chamber allows for the metered volume of fluid to be ejected through the second valve when opened, by pressurising the metered volume. In some embodiments, the elasticity of the resilient or compliant chamber will provide the pressurising means to empty the metering chamber once the second valve is opened. The metering chamber may take the form of bellows, bellows bottle, sprung bellows, an elastic membrane, resilient diaphragm or flexible container, such as a bag, amongst other suitable compliant or resilient means. As an alternative, an arrangement of a piston and cylinder may be used to create compliance.

In one aspect, the compliant or resilient chamber itself defines the volume of the metering chamber. In an alternative aspect, the metering chamber further comprises a fixed element. The fixed element may be arranged to constrain the volume into which the compliant or resilient chamber may expand. In this case, the metered volume is determined by the volume provided by the fixed element. The fixed element may take the form of a box, cage, frame, or other suitable format. The elasticity of the compliant or resilient chamber provides the means to pressurise the metered volume, and eject the fluid once the second valve has opened.

In various embodiments the fluid in the metering chamber is pressurised by mechanical pressure. The metering chamber may have, for example, a piston or diaphragm device with a spring behind it. It will be appreciated that the spring should exert a lower pressure in the resilient metering chamber than that at the exit from the containment volume in order that the fluid flows to fill the metering chamber. In this embodiment, as the fluid enters the metering chamber from the containment volume, it is at a pressure sufficient to push back the piston or diaphragm in order to fill the metering chamber with the correct volume. When the second valve is opened, the piston or diaphragm moves back into position and forces the fluid out of the second valve. As an alternative to a movable piston or diaphragm, or in addition thereto, a closed adjacent chamber could be provided, with a connection from behind the piston or diaphragm to the adjacent chamber, whereby air or other gas in the adjacent chamber acts as a spring on the piston or chamber. Where neither piston nor diaphragm is provided, a float valve, such as a seat and buoyant ball, can close airflow from the metering chamber to the adjacent chamber, thereby providing that the chamber fills to a metered volume only.

In various embodiments the fluid in the metering chamber is pressurised by gas means. These means could be compressed gas/air or propellant. For example, if the metering chamber is a flexible bag container, means to compress this would include pressurised gas.

In forms of the invention, the two, first and second, valves may be co-ordinated by being ganged together. The first and second valves may thus be simply co-ordinated, for example by being linked together. The valves may be part of the same component and thus be linked in their movement, or be made or moulded together, with the shape and movement providing the co-ordination required; only one valve is open at any time.

In one alternative, the valves may be spring-biased such that the first valve is normally open to fill the metering chamber and closed for dispensing when the second valve is opened. Alternatively they can be spring biased for the first to be normally closed with pressure against the spring bias, the bias being acted against to fill the chamber and released for dispensing. The spring bias need not be provided where the ganged valves are moved between their states by different manually operated features, such as opening of a closure means opening the first valve and pressing of a release button dispensing the fluid.

Conveniently the valves are kink valves in tubes leading from the containment exit to the metering chamber from the metering chamber to the outlet. In the embodiments described below, the kink valves are opened and closed by pivoting a central portion of tube between the valves, or at least a connector having the tubes connected to it. However, it can be envisaged that the valves could be opened and closed by sliding the central portion of tube or the connector. For clarification, a kink valve is formed by a piece of flexible tube that is moved between an open, un-obstructed state and a closed state in which the tube is bent to a state in which its opposite walls collapse against each other with the result that the tube is obstructed and fluid cannot flow through it.

In an alternative embodiment discussed below, the two valves are kink valves, wherein the two valves are manufactured as a single component. A separate component forming the metering chamber may be used to connect the two valves. In this embodiment, the two valves may be moulded as two straight tubes that sit adjacent and parallel to each other. After moulding, the valves are kinked with the kinks being formed by folding one tube down from the top and the second folded up from the bottom. This leaves one fixed (i.e. immobile) tube pointing up to attach to the containment volume and the other fixed tube pointing down to the dispensing outlet. The two mobile tubes may be linked with the metering chamber. The metering chamber may be a separate component, such as a snap on component. In one aspect, the metering chamber can be arranged to join the two mobile tubes with an offset between them such that the angle of bend in each tube is never the same. In another aspect, the two mobile tubes may be joined without an offset. This would mean that they could both be bent at 90 degrees (for example) at the same time. An offset might be used to ensure that one tube is always bent to a closed position before the other tube is straightened sufficiently for the bore of the tube to allow passage of fluid along it.

Moving the metering chamber with reference to a fixed component such as the dispensing outlet will cause a metered volume of liquid to be dispensed. The force to move said chamber will depend upon the tube characteristics and is intended to be small. For example, moving the component towards the dispensing outlet causes the metering chamber to fill, moving the chamber away from the dispensing outlet causes a metered volume of liquid to be dispensed. The metering chamber may be moved using any suitable manually operated means, for example, it can be linked or connected to an actuator on the external surface of the metering device.

As used herein, the term fluid refers to a substance that is capable of flowing, for example a liquid or a gas, or a suspension of solid particles.

To help understanding of the invention, embodiments thereof will now be described by way of example only and with reference to the accompanying drawings, in which.

Figure 1:
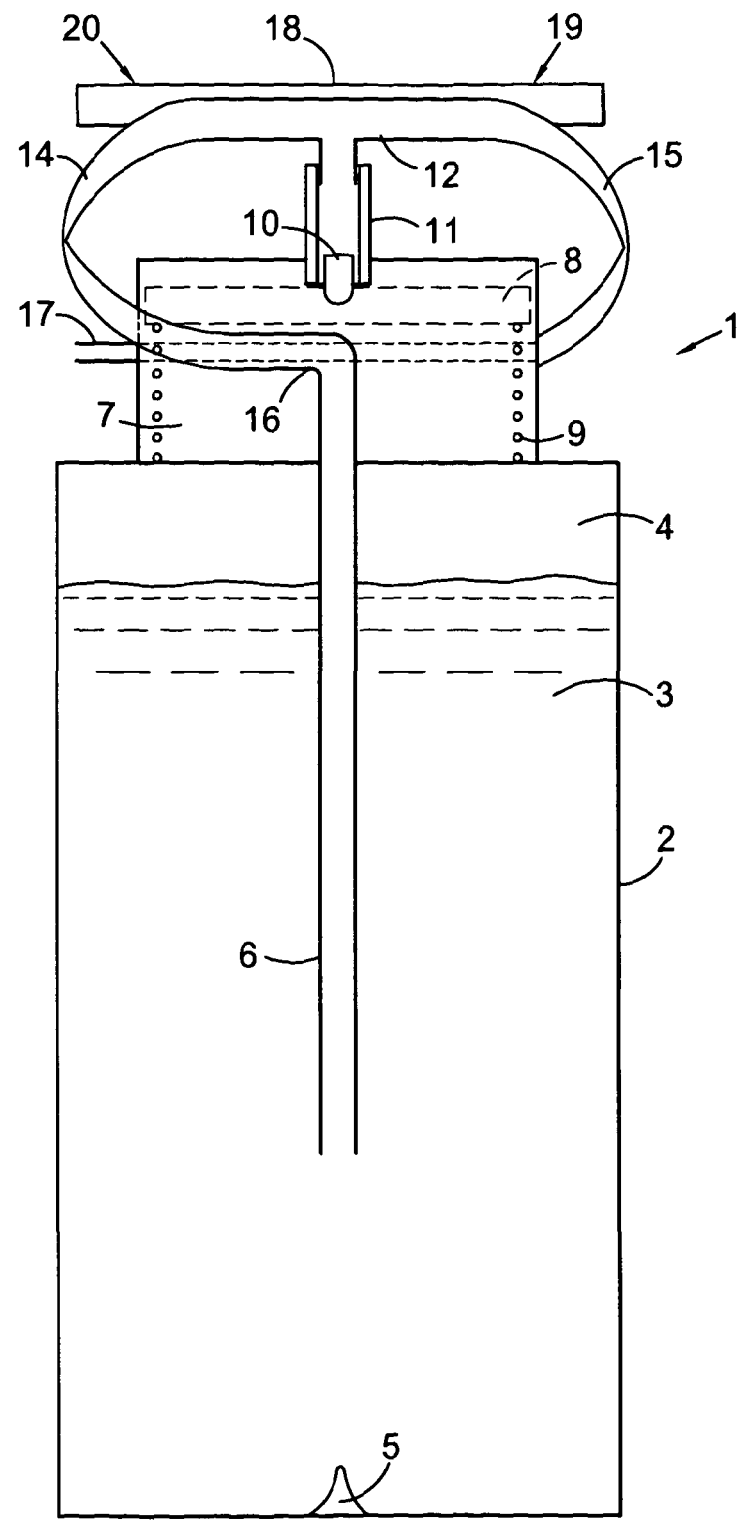
FIG. 1 is a diagrammatic side view of a first container according to a form of the invention.

Referring to first to FIG. 1, a dispenser 1 comprises a main container 2 of liquid 3 to be dispensed, the liquid being under pressure from a gas 4 above it and introduced via a valve 5 in the bottom of the container. A rigid supply tube 6 extends up from the liquid and out of the top of the container, which is sealed around it. On top of the container 2 and to one side of the tube 6, a metering chamber 7 is provided. It has a piston 8 in it over a light spring 9. A connection 10 extends out of the side of the chamber and is connected by a resilient, relatively thick tube 11. This carries a tee piece 12 at its upper end.

Two relatively thin elastomeric tubes 14, 15 extend in opposite directions from the tee piece 12. One is curved back to an angled top 16 of the tube 6 and the other is curved in the other direction to the inner end of a spout 17. The length and radius of curvature of the thin tubes is such that they are both kinked in the position shown in FIG. 1.

For use, a toggle 18 on top of the tee piece is first pressed on its end 19 remote from the spout 17 for, in some examples, five seconds. This gives sufficient time for the liquid to be propelled up the tube 6, through the tube 14, which is now un-kinked, and into the metering chamber 7. Here its pressure acts on the piston and overcomes the spring 9. The piston is displaced and the chamber fills. Within a short period of time, in some examples 5 seconds, it is full. The user then releases the toggle and the tee piece is centred by the resilience of the resilient tube 11. The tubes 14, 15 remain kinked.

In this form of the invention, finger pressure now applied to the other end 20 of the toggle pivots the tee piece in the other direction and causes the kink in tube 15 to open. The spring 9 now acts via the piston to drive the liquid out of the spout 17, delivering a metered dose of the liquid.

It will be appreciated that only light force by the user is required, in this form of the invention to operate the toggle and that this force is not related to the pressure of the liquid, nor indeed its viscosity. All the energy for causing the liquid to flow is released from the pressure of the propellant gas in the container.

Figure 2:
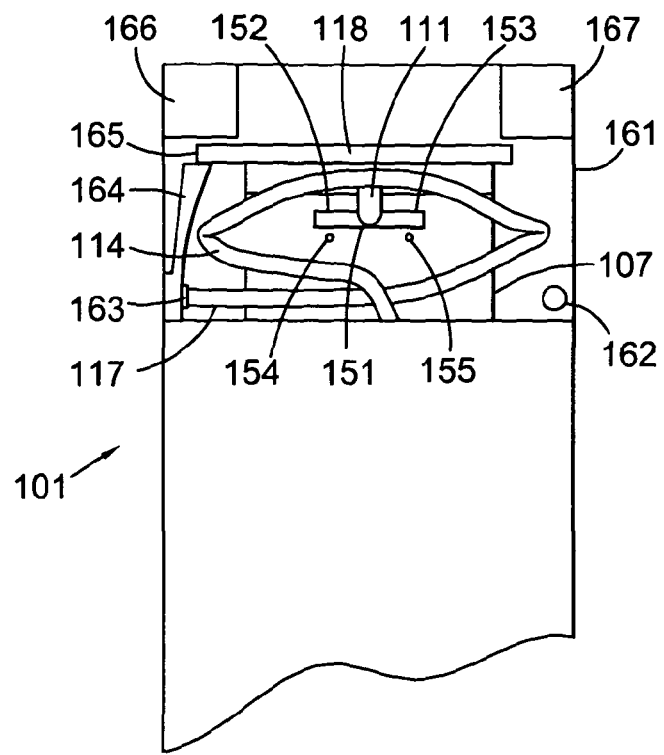
FIG. 2 is a similar view of a second container according to a form of the invention, with a closure cap closed.
Figure 3:
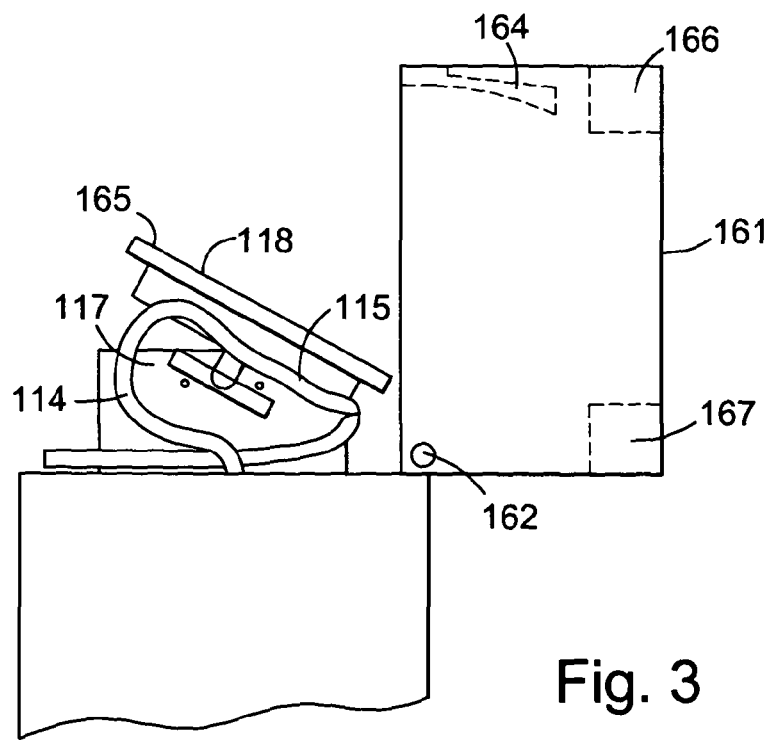
FIG. 3 is a side view of the second container with the cap open and dispensing valves moved to their position for charging a metering chamber.
Figure 4:
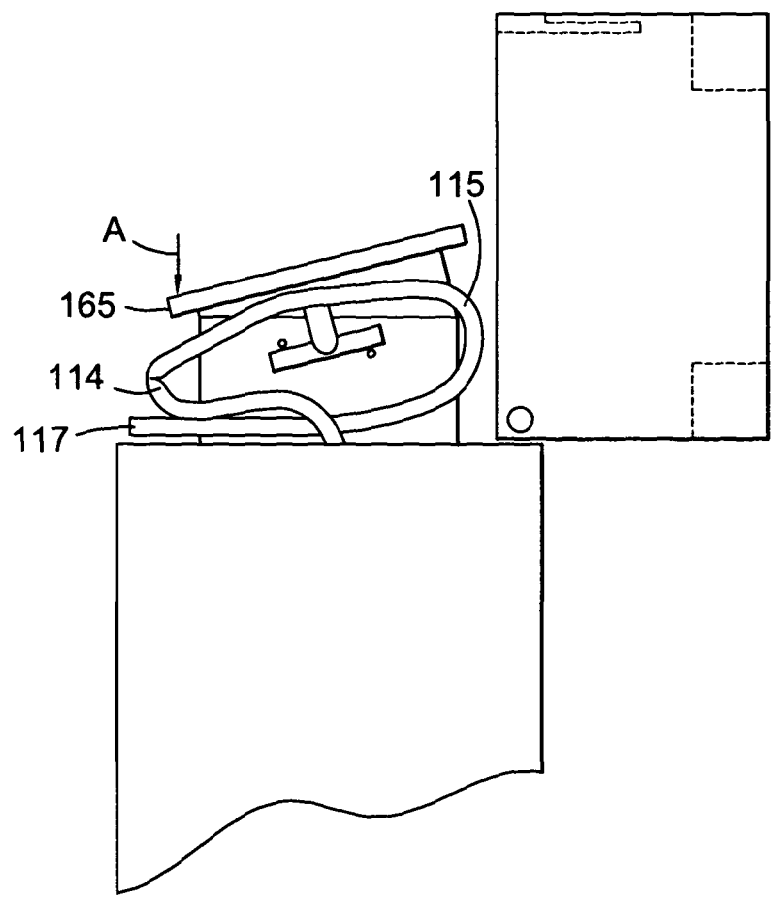
FIG. 4 is a similar view with the valves moved to the dispensing position.

Referring on FIGS. 2 to 4, the dispenser 101 there shown is basically the same as the dispenser 1. However two modifications are introduced:

In this embodiment, the tube 111 connecting the tee piece to the metering chamber 107 is rigid, with the connection 151 into the chamber being a pivotal connection, with sufficient sealing to withstand the pressure of the contents of the container. The tube has two fingers 152,153, which co-operate with the detents 154,155 on the side of the chamber.

In this embodiment, the dispenser is provided with a pivoted cap 161. This pivoted 162 remote from the spout. A pad 163 inside the cap closes the end of the spout when the cap is closed as shown in FIG. 2. In this position, a detent 164 integral with the cap has sprung passed the nose 165 of the toggle 118 and engages under it. An abutment 166 holds the nose down, that is with the kink in the tube 114 held closed. A further abutment 167 bears on the other end of the toggle to urge the nose past the detent 164. A clip on the rim of the cap engages the rim of the container and holds it closed. The finger 152 and detent 154 also hold the tube closed.

When the cap is pivoted open, the tee piece is pulled up by the detent 164, which clears the toggle nose. The finger 153 and detent 155 hold the tee piece in its other position, that is, with the tube 114 now open and the tube 115 (not labelled on FIG. 2 but shown on FIG. 3) kinked. The liquid in the container can now flow into the chamber 117. In some forms of the invention some time will elapse between opening of the cap and the user dispensing the liquid. This allows time for the chamber to fill. When the toggle is depressed at its nose 165, as shown in FIG. 4 by arrow A, the kinking state is reversed and the liquid is dispensed through the spout. The finger 152 and detent 154 hold the tee piece in position until the cap is re-closed. Nevertheless, a second dispensing of fluid with the cap open is possible by recharging the chamber with pressure on the other end of the toggle to change the state of the kinks. The position of the metering chamber relative to the containment volume may be varied in forms of the invention. For example, it may be placed on top of the containment volume or beside it. In other examples the metering chamber may be placed on top of the containment volume and sized so that it appears to form a continuous shape, for example, a cylinder. In some embodiments the metering chamber may provide a reassurance that it is full by means of indicia showing, for example, the temperature of its contents or simply by means of a transparent or translucent area so that contents within can be seen.

Figure 5:
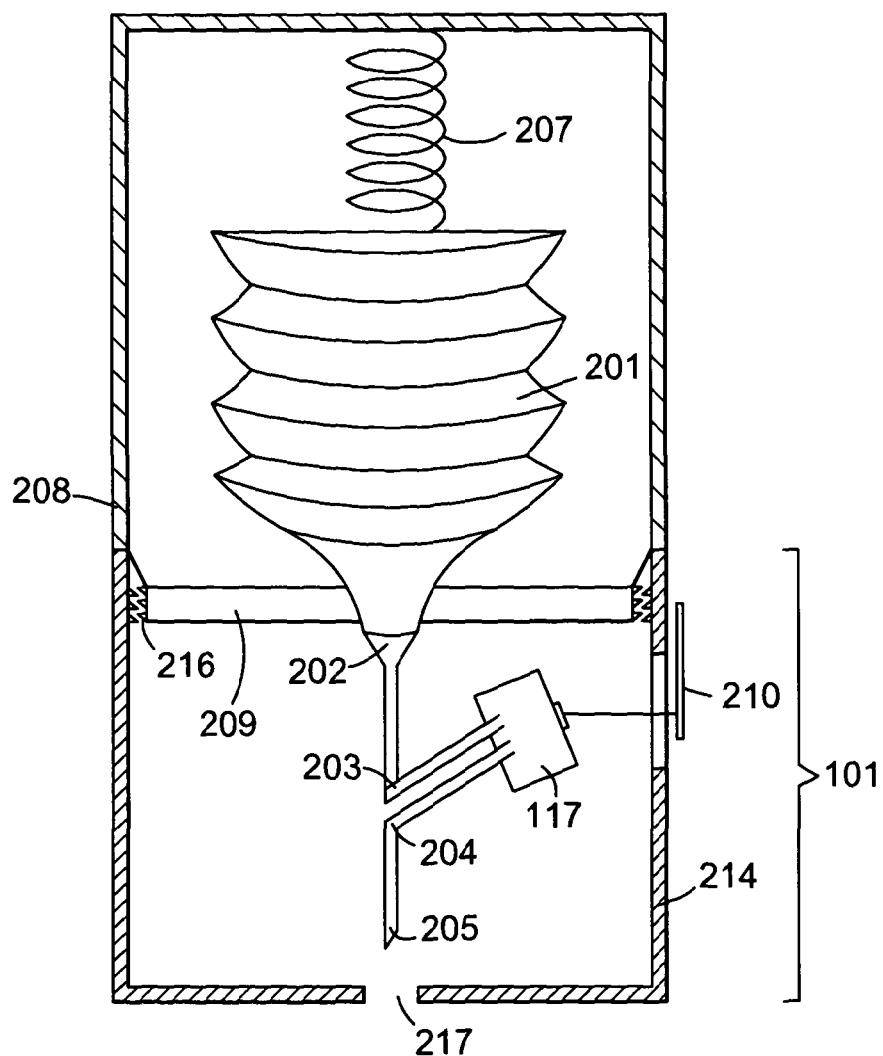
FIG. 5 is a diagrammatic view of a metering device according to another form of the invention, which may be used with a separate containment volume as shown.
Figure 6:
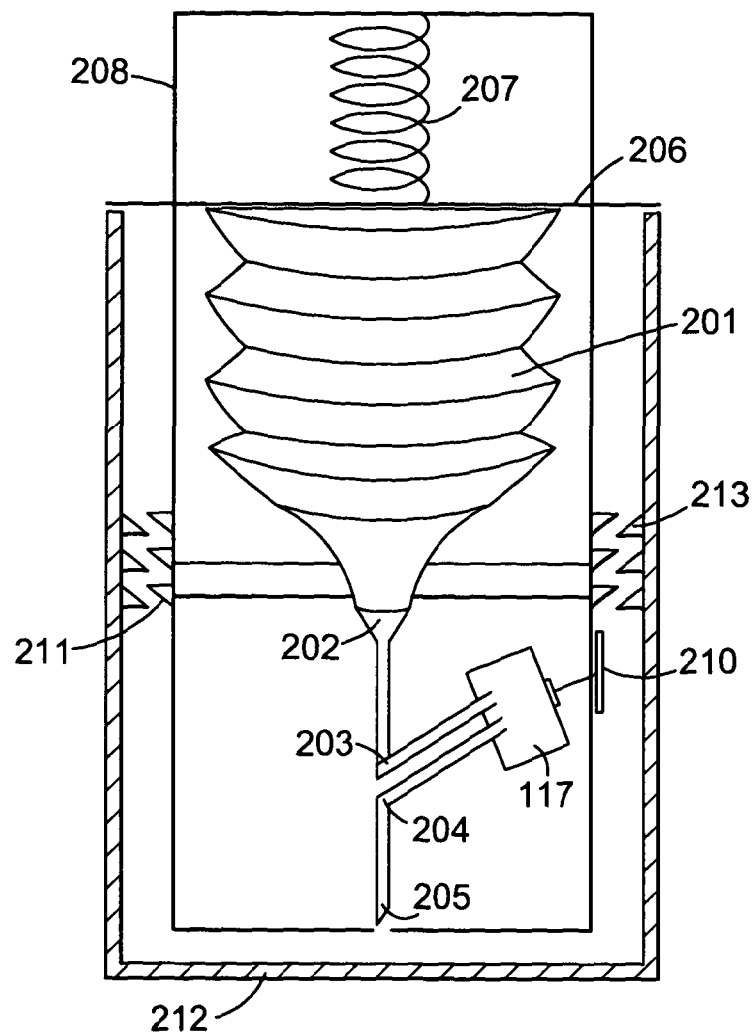
FIG. 6 is a representation of a third container according to one form of the invention, showing the operation of the closure cap which releases the spring.

Referring to FIGS. 5 and 6, there is shown another form of the invention, shown as two related variations. In either form, the containment volume is provided within a bellows bottle 201 with an exit from the containment volume 202, a first valve 203 provided by a tube which can be kinked, connected to a metering chamber 117, which is turn is connected to a second valve 204 provided by a second tube which can be kinked. The second valve has a dispensing outlet 205 through which the fluid is dispensed. There is provided a spring 207, the spring is linked to the container 208, and either to the bellows bottle 201 directly (FIG. 5) or to a diaphragm device (206 on FIG. 6). The bellows bottle is supported on a plinth 209, through which the exit 202 extends. In operation, the spring 207 (and diaphragm 206 if used) arrangement exerts a pressure upon the bellows bottle 201, such that when the first valve 203 is open, the fluid within the bellow bottle 201 is forced to flow through the exit from the containment volume 202 into the metering chamber 117. Once the metering chamber 117 volume has been filled, no further flow of fluid from the bellows bottle 201 may occur. During filling of the metering chamber, the second valve 204 is closed. Only one valve is open at any time.

The metering chamber 117 is linked to an actuator 210 on the outside of the dispenser 101. The metering chamber is linked to the two kink valves 203 and 204. In use of either form of the invention, the user manually operates the actuator 210 by sliding it up and down in the vertical axis. This in turn causes the metering chamber to pivot around the two kink valves on the same axis. This closes the first kink valve 203 and opens the second kink valve 204. As the metering chamber 117 is compliant, it returns to the original unfilled volume, forcing the fluid within it to exit via the dispensing outlet 205. As the actuator 210 is returned to the original position, the metering chamber pivots again about the two kink valves and the second kink valve 204 closes and the first kink valve 203 opens, allowing the metering chamber to be filled again. In this aspect, it is envisaged that the metering chamber 117 has already been filled before the user wishes to dispense a metered volume of fluid. However, the operation of the actuator 210 could also work vice versa, causing the metered chamber 117 to be filled by closing the second valve 204 and opening the first valve 203, followed by closing the first valve 203 and opening the second valve 204 to the exit 205. The force required to move the actuator 210 will be small. In one form, moving the actuator 210 towards the dispensing outlet 205 causes the metering chamber 117 to fill, moving the actuator away from the dispensing outlet 205 causes the fluid to be dispensed from the metering chamber 117. Although not shown on the diagram, it is possible to spring bias the mechanism of actuation. In a preferred aspect, the mechanism is biased towards the dispensing outlet 205 so that a low-force movement is required to dispense the metered volume, Releasing the actuator 210 allows it to return to its biased position, allowing the metering chamber 117 to be filled ready for the next dispense.

In FIG. 5, there is provided a metering device 101 which can be attached as shown to a containment volume as required. In this aspect, the container can be disposable after use, and the metering device 101 reusable. The metering device 101 in this aspect comprises a receptacle 214 which houses the metering chamber 117 linked to two valves 203 and 204 and additionally linked to an actuator 210 on the outside of the receptacle 214. The receptacle may have an opening 217 through which the fluid is dispensed. The receptacle has internal threads 215. In this form of the invention, the containment volume is presented in a container 208 which has external threads 216 present on the outer surface. In use, the metering device 101 is attached to the container 208 by virtue of the internal screw threads 215 which receive and hold the external screw threads 216 on the container 208. The exit from the containment volume 202 is provided with the metering device 101. It is connected to the containment volume by virtue of the metering device 101 being attached to the container 208 via the screw threads 215 and 216. In this form of the invention, the containment volume may be provided with a seal, which may be punctured as the metering device is screwed onto the container. For example, the exit from the containment volume may be provided with means to reversibly attach to the containment volume, and this exit is held rigidly in the metering device.

In FIG. 6, there is provided a container for fluid material to be dispensed, the container 208 is provided with external screw threads 211. A closure cap 212 is provided with internal screw threads 213 which receive and hold the external screw threads 211 on the container 208. The closure cap 212 and container 208 are turned relative to each other when the closure cap 212 is attached. This motion can be linked to the spring 207, and attaching the closure cap 212 to the container 208 can result in the spring 207 being lifted or releasing, reducing or removing the pressure of the spring and diaphragm 206 on the bellows bottle 201. In the version represented in FIG. 6, this is achieved by the closure cap 212 interacting with the diaphragm 206. When the closure cap 212 is removed by disengaging the screw threads 211 and 213, the spring 207 returns back into position, together with the diaphragm 206, in order to exert pressure on the bellows bottle 201 and the fluid therein. It would be understood that this could also work in the opposite direction if required. It will also be appreciated that attaching the closure cap 212 to the container 208 prevents accidental operation of the actuator 210, effectively locking it in a fixed position.

In an alternative embodiment, in order to reduce or remove the pressure on the containment volume during periods of no use, there may be included a third valve between the exit from the containment volume and the metering device.

Figure 7A:
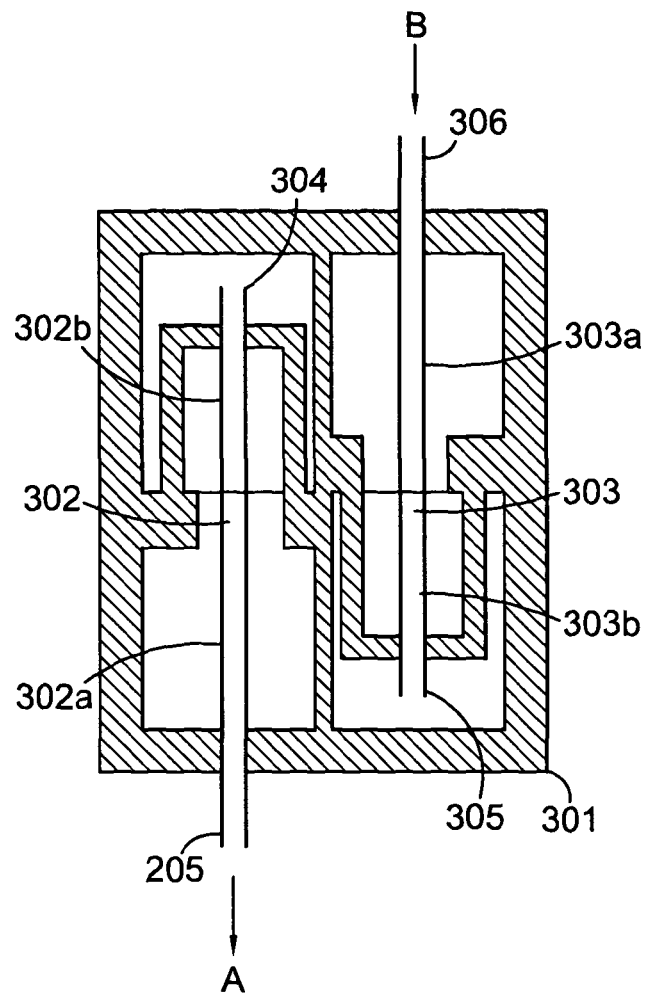
FIG. 7 is a representation of one form of the kink valves that may be used according to the invention.

As shown in FIG. 7a, the valves for any aspect of the invention can be produced as a single component 301. A separate component (not shown) can be used to join the two valves and provide the metering chamber. The single component 301 can be moulded as a one part two kink valve component. The kink valves are effectively moulded as two tubes 302 and 303 that are adjacent and parallel. The first tube 302 forms the second kink valve. The arrow A shows the direction of the flow of fluid through the tube 302, to the dispensing outlet 205. At the other end of the tube 304, the separate component is linked. The other tube 303 provides the first kink valve. Fluid flows in from the exit 306 from the container volume and through the tube 303 into the metering chamber (not shown) connected at the other end of the tube 305. In order to put a kink in the valves, the component 301 is modified by folding one tube 302 down from the top and the second tube 303 up from the bottom. This leaves one fixed (immobile) tube 303a pointing up to attach to the containment volume (not shown) and the other fixed tube 302a pointing down to act as the dispensing outlet. The two mobile tubes 302b and 303b are linked to a separate component which provides the metering chamber (not shown). This separate component may simply snap on. The separate component can be arranged to join the two mobile tubes 302b and 303b with an offset between them, such that the angle of bend in each tube is never the same. An offset would ensure that one tube was always bent to a closed position before the other tube was straightened sufficiently to allow fluid to flow. However, it will be appreciated that the two tubes 302b and 303b can be joined without any offset, and alternative means can be used to kink the valves appropriately.

Figure 7B:
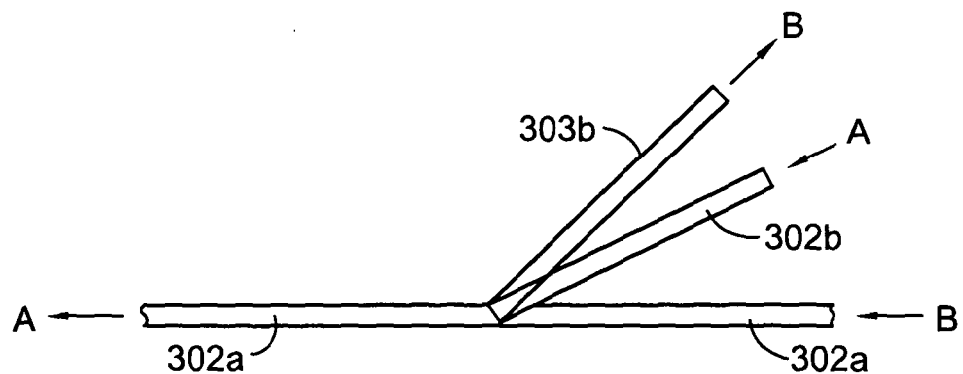

FIG. 7b shows a depiction of the tubes; both tubes 302 and 303 are provided with immobile 302a and 303a and mobile sections 302b and 303b. Arrows A show the flow of fluid through the first tube 302 which depicts flow from the metering chamber to the dispenser outlet and arrows B show the flow of fluid through the second tube 303 which depicts flow from the containment volume exit to the metering chamber—on the premise that the kink has been removed sufficiently to allow the fluid to flow.

In other embodiments the present invention provides a metered dose drug delivery device. This provides a containment volume of the drug, in some forms this comprises a can, and for example a metallic can. An exit from the containment volume through which the fluid is pressurised above ambient pressure is also present. In addition a metering chamber sized at the required dosage (or fraction thereof) of the drug is provided, for example attached to the containment volume. In the form of the invention in which the metering chamber is a fraction of the required dosage it may, for example be half the required dosage and the user provided with instructions indicating that two usages of the drug delivery device will be required to achieve the required dose. In other case the metering chamber may provide a dosage that is the required amount of drug, for example, 5 millilitres.

The invention thus extends to:

A metered dose drug delivery device comprising:

a containment volume of the drug;

an exit from the containment volume through which the drug is pressurised above ambient pressure, a metering chamber sized at the required dosage (or fraction thereof) of the drug, a first valve for allowing a dose of the drug to flow from the exit into the metering chamber and fill the chamber to meter the dose (or fraction of the dose), a dispensing outlet open to ambient pressure, a second valve allowing the drug in the metering chamber to flow from metering chamber to the dispensing outlet and manually operable means for co-ordinating action of the valves whereby when the first valve is open for filling the metering chamber the second valve is closed and vice versa.

Similar to other forms of the invention there is also provided a first valve for allowing a dose of the drug to flow from the exit into the metering chamber and fill the chamber to meter the dose (or fraction of the dose), and a dispensing outlet open to ambient pressure. Further there is a second valve allowing the drug in the metering chamber to flow from metering chamber to the dispensing outlet with manually operable means for co-ordinating action of the valves whereby when the first valve is open for filling the metering chamber the second valve is closed and vice versa. The drug may be dispensed into a transfer device such as a teaspoon or directly into the mouth of a user. When the drug delivered is to be used as a lotion or medicament, it is delivered directly on the skin, eyes or mucosal membranes of the user or patient.

In order to provide reassurance to a user that the correct dose has been dispensed there may also be present means to indicate that the metering chamber has filled, in some cases this may comprise simply a translucent or transparent area.

The invention is not intended to be restricted to the details of the above described embodiments. For instance, whereas in these embodiments the valves have a quiescent state in which both are closed and the metering chamber is empty, being filled on first actuation to open the first valve, in an alternative the first valve is open in the quiescent state, with metering chamber charged ready for dispensing movement of the valves. This is a two-stage process, with firstly the closing of the first valve to the main container and secondly the opening of the second valve to the outlet. This sequential operation can be effected against a light spring force, the spring returning the valves to that quiescent state after dispensing. Another possibility is that the two valves could be closed in the quiescent state, with the metering chamber having been filled or charged by opening of the first valve immediately after a previous dispensing action. In one form of the invention, the second valve needs only to be opened for dispensing.

Again, whilst some of the above described embodiments, the metering chamber is attached to the top of the main container, with its piston movable in it; it can also be envisaged that the metering chamber could be movable with actuation of the valves, either in translation or rotation, as depicted in other embodiments.

Further, embodiments of the present invention may be used to meter and dispense such things as liquids, for example medicines, shampoos, soaps, creams or other substances. Further, embodiments of the present invention, may, with suitably chosen materials and sealing valves, dispense other fluids such as gases and, if sufficiently mixed, solids suspended in a fluid, particularly liquids, may also be metered and dispensed.

The above disclosure is intended to be illustrative and not exhaustive. This description will suggest many variations and alternatives to one skilled in the art to which the invention relates. Each and every of these alternatives and variations are intended to be included within the scope of the following claims where the term "comprising" means "including, but not limited to". Those familiar with the art may recognize other equivalents to the specific embodiments described herein which equivalents are also intended to be encompassed by the claims.

Having described particular embodiments of the present invention, it is to be appreciated that the embodiments referred to are exemplary only and that variations and modifications may be made without departing from the scope of the invention as set forth in the appended claims. Those skilled in the art may recognize other equivalents to the specific embodiment described herein which equivalents are intended to be encompassed by the claims attached hereto.

The invention claimed is:

1. A metering device for fluids from a containment volume, the metering device comprising:
   an exit from the containment volume;
   pressurizing means for pressurizing the liquid through the exit,
   an expansible metering chamber,
   a first kink valve for allowing a dose of the fluid material to flow from the exit into the metering chamber and fill the chamber to meter the dose, a dispensing outlet open to ambient pressure,
   a second kink valve allowing the fluid material in the metering chamber to flow from metering chamber to the dispensing outlet and
   manually operable means for co-ordinating action of the first and second kink valves whereby when the first kink valve is open for filling the metering chamber the second kink valve is closed and vice versa,
   wherein the metering chamber is resiliently biased in a first condition having a first volume and is expansible to a second condition having a second volume, greater than the first volume such that when the second kink valve is opened the metering chamber reverts from the second condition to the first condition to urge the contents of the metering chamber through the dispensing outlet.

2. A metering device for fluids from a containment volume as claimed in claim 1 wherein the fluid material is pressurised above ambient pressure by means of a propellant separated from the fluid material by separation means.

3. A metering device for fluids from a containment volume as claimed in claim 1 wherein the fluid material is pressurised above ambient pressure by means of a resilient diaphragm.

4. A metering device for fluids from a containment volume as claimed in claim 1 wherein the expansible metering chamber is a diaphragm, elastic membrane, bellows bottle or flexible container.

5. A metering device for fluids from a containment volume as claimed in claim 1 wherein the device is a metered drug delivery device and the fluid is a drug.

6. A metering device for fluids from a containment volume as claimed in claim 5 wherein the metering chamber volume when in the second condition is the required dose of the drug, or a fraction thereof.

7. A container for fluid material to be dispensed in metered doses, the container comprising:
   an expansible containment volume resiliently biased in a first condition having a first volume and expansible to a second condition having a second volume, greater than the first,
   an exit from the containment volume;
   pressurizing means for pressurizing the liquid through the exit,
   a metering chamber,
   a first kink valve for allowing a dose of the fluid material to flow from the exit into the metering chamber to expand the chamber to the second condition and fill the chamber to meter the dose, a dispensing outlet open to ambient pressure,
   a second kink valve allowing the dose of fluid material in the metering chamber to flow from metering chamber to the dispensing outlet upon reversion of the expansible chamber to the first condition such that the dose is urged towards the dispensing outlet and manually operable means for co-ordinating action of the first and second kink valves whereby when the first kink valve is open for filling the metering chamber the second kink valve is closed and vice versa.

8. A container for fluid material to be dispensed in metered doses as claimed in claim 7 wherein the fluid material is pressurised above ambient pressure by means of a propellant separated from the fluid material by separation means.

9. A container for fluid material to be dispensed in metered doses as claimed in claim 7 wherein the fluid material is pressurised above ambient pressure by means of a resilient diaphragm.

10. A container for fluid material to be dispensed in metered doses as claimed in claim 7 wherein the expansible chamber is a diaphragm, elastic membrane, bellows bottle or flexible container.

11. A metering device for fluids from a containment volume, the metering device comprising:
    an exit from the containment volume through which the fluid material is pressurised above ambient pressure,
    an expansible metering chamber,
    a first kink valve for allowing a dose of the fluid material to flow from the exit into the metering chamber and fill the chamber to meter the dose, a dispensing outlet open to ambient pressure, a second kink valve allowing the fluid material in the metering chamber to flow from the metering chamber to the dispensing outlet and manually operable means for co-ordinating action of the valves whereby when the kink valve is open for filling the metering chamber the second kink valve is closed and vice versa, wherein the metering chamber is resiliently biased in a first condition having a first volume and is expansible to a second condition having a second volume, greater than the first volume such that when the second kink valve is opened the metering chamber reverts from the second condition to the first condition to urge the contents of the metering chamber through the dispensing outlet.

* * * * *